United States Patent [19]

Boehringer et al.

[11] 4,046,014

[45] Sept. 6, 1977

[54] SEALABLE ACTIVATED CHARCOAL GAS SAMPLER

[76] Inventors: John R. Boehringer, 427 Parkview Drive; John Lecky, 501 Shortridge Ave., both of Wynnewood, Pa. 19096

[21] Appl. No.: 656,258

[22] Filed: Feb. 9, 1976

Related U.S. Application Data

[63] Continuation-in-part of Ser. No. 588,772, June 20, 1975, abandoned.

[51] Int. Cl.$^2$ .............................................. G01N 1/22
[52] U.S. Cl. ................................................ 73/421.5 R
[58] Field of Search ................... 73/421.5 R, 422 GC, 73/23; 23/232 R, 254 R

[56] References Cited

U.S. PATENT DOCUMENTS

| | | | |
|---|---|---|---|
| 1,715,854 | 6/1929 | Martyn | 285/DIG. 18 |
| 3,311,454 | 3/1967 | Kemeny et al. | 73/23 X |
| 3,505,022 | 4/1970 | Luckey | 23/232 R |
| 3,522,009 | 7/1970 | Borkenstein | 23/232 R |

Primary Examiner—Jerry W. Myracle
Attorney, Agent, or Firm—Paul & Paul

[57] ABSTRACT

A rigid reuseable metallic tube is provided with sealing screws at either end, operable to deform malleable lead washers against a labyrinth pattern at the extreme tube ends. In one embodiment, a wire form is disposed within the tube with an annular portion conforming to the tube interior, and an elongated wire depending therefrom, for holding the charcoal in place. In another embodiment, wire screen discs hold the charcoal in place, and utilize elongated pegs to remove the screen and withdraw the charcoal. Plugs of glass wool may also be used to enclose the activated charcoal against the annulus and/or the screens. An orifice in the tube may be provided to restrict air flow through the charcoal. Alternatively, a needle valve and flow meter may be used to regulate flow. An alternative embodiment is reuseable, and utilizes sintered metallic plugs press fit into and against the metallic tube, thereby giving rise to advantageous methods for removal of the sampled gases.

11 Claims, 13 Drawing Figures

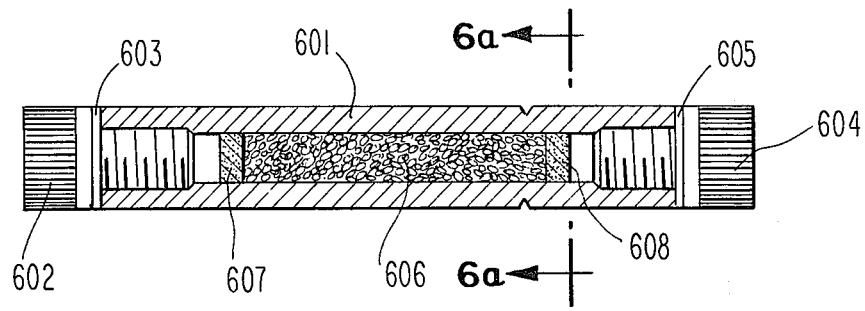
Fig. 6
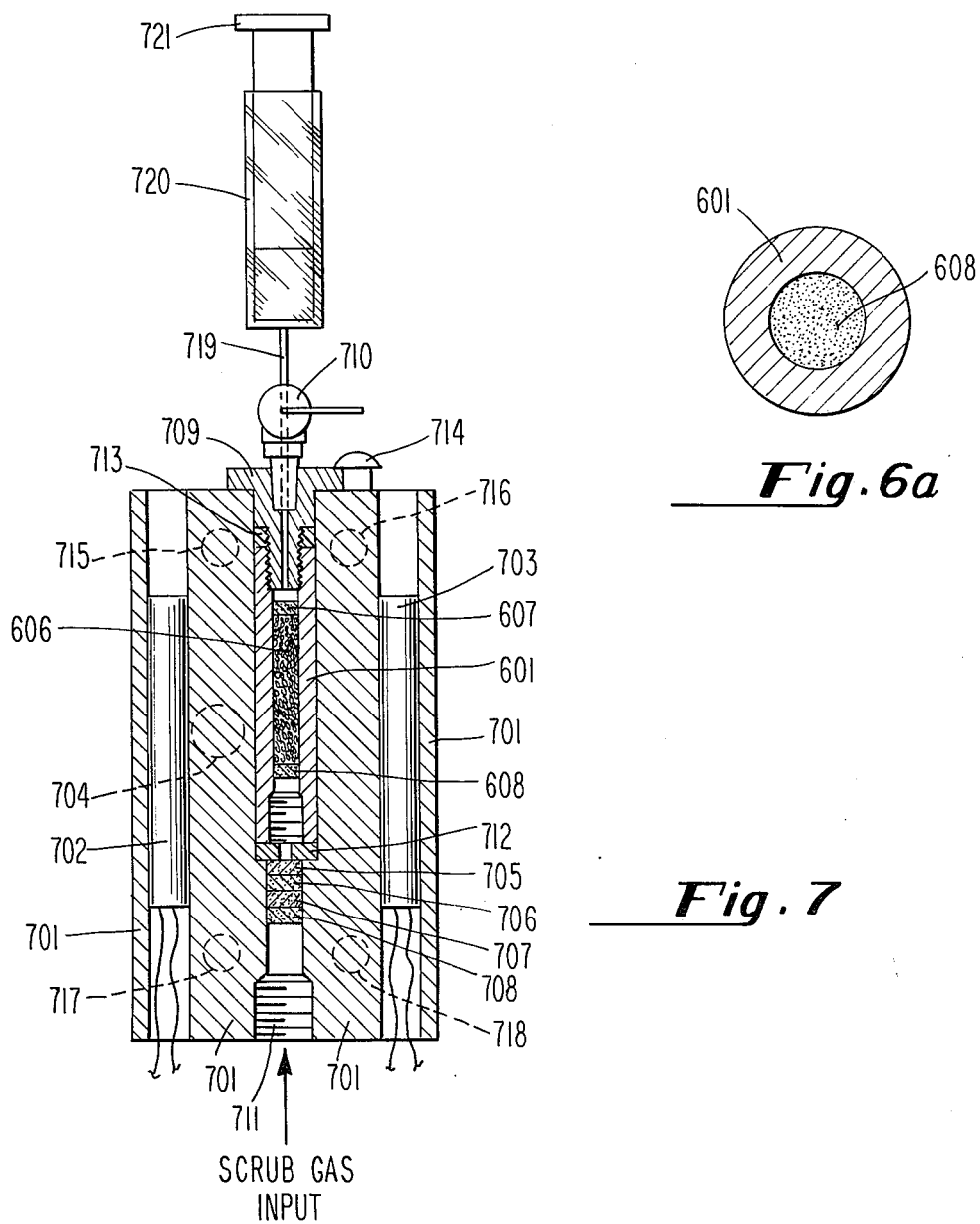
Fig. 6a
Fig. 7
SCRUB GAS INPUT

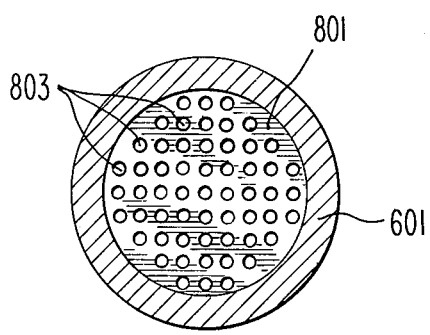
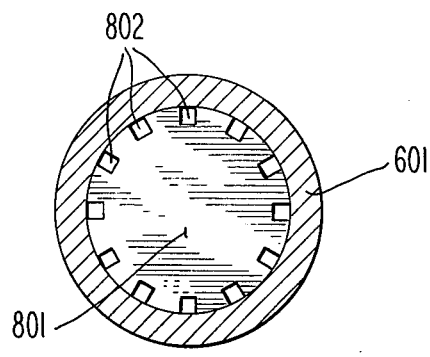
Fig. 8a    Fig. 8b
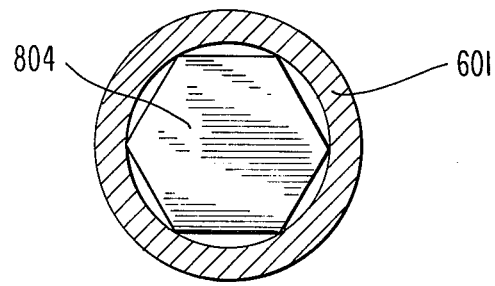
Fig. 8c

SEALABLE ACTIVATED CHARCOAL GAS SAMPLER

CROSS REFERENCE

This is a continuation-in-part of copending U.S. application Ser. No. 588,772, filed June 20, 1975 now abandoned.

BACKGROUND OF THE INVENTION

This invention relates to air sampling devices, and more particularly to sealable cartridges for time averaged sampling of ambient gases.

Concomitant with increasing public and industrial awareness of the deleterious effects of many gases heretofore thought relatively harmless, substantial efforts are being allocated to detection and elimination of the harmful gases. In accordance with the Occupational Safety and Health Act of 1970, Public Law 91-596, Dec. 29, 1970, 84 Statutes 1590, specific exposure limits are set forth for protection of workers. These standards are based on total exposure over an entire working shift, i.e., based on time weighted averages. In accordance with the legislation, compliance is monitored by drawing a known quantity (e.g., one liter) of ambient gas per hour for eight hours through a tube packed with charcoal. The contaminant gases are absorbed by the charcoal which later is eluted, on one of a variety of ways (e.g., with carbondisulfide solvent), and analyzed such as by a gas chromatograph, mass spectrograph, or analogous analytic methods.

Consequently, employers and the like who are required to meet these requirements (and to pass periodic testing by labor department officials) have need to monitor their working conditions on an ongoing basis, in an effective a manner as possible.

It is accordingly a general object of the present invention to provide apparatus useful for monitoring time weighted average exposure (commonly referred to as "TWA") in accordance with legislated standards.

The most common method presently utilized to obtain time weighted average exposure is to draw the gases through a glass tube packed with charcoal. Typically, the tubes are filled with alternate segments of activated charcoal and glass wool or the like, are often provided with a precision locking spring and porous polyurethane plugs to hold the material in place, and are drawn and sealed at either end. For use, the drawn tips are broken off, after which flexible plastic sealing caps are mounted over the drawn portion.

The glass tube samplers involve substantial inconveniences, safety problems, and functional difficulties. Most obviously, the use of glass brings about the danger of breakage and cutting, both in use while breaking off the ends, and in shipment to the user. Perhaps even more importantly, use of drawn glass tubes involves resealing difficulties, should the sealing caps fit improperly to be mounted improperly by the user. Further, such caps must be of a flexible material of which all the known elastomers have some absorption characteristics with the gases being sampled. In either case, contamination of the charcoal or loss of the trapped gas sample may result by leakage, absorption, or adsorption, thereby obviating the accuracy of the measurements.

In order to avoid contamination or loss of the sample during shipment to an analysis facility, it is often necessary to utilize dry ice containers, which serve to maintain the gases on the charcoal. This method is impractical, costly, incovenient, and inaccurate. Nevertheless, the flexible seal must be used on the tubes because of resealing of the tube by melting would produce too much heat, which would drive off the captured gases. Furthermore, rigid seals are inapplicable, because round glass tubing is neither sufficiently round nor concentric to cooperate effectively with screw seals. A sealed metal container could be used for the tubes, but this introduces air spaces into which entrapped gas could migrate.

Further disadvantages of the glass seal method are the requirement for spring locks, or the like, to hold the charcoal in place in the tube. A further disadvantage is the difficulty of removing the batches of charcoal effectively when the time for analysis occurs.

It is an object of the present invention to provide a gas sampling cartridge which is unbreakable, and effectively reuseable and resealable by recharging with fresh charcoal at the manufacturer thus keeping costs to a minimum.

It is a further object to provide effective yet relatively economical apparatus for holding charcoal in place in the cartridge, during shipment and use.

It is another object to provide air sampling cartidges which may be effectively interconnected one to the other in order to handle heavier concentrations which would saturate one tube, and thereby to meet a large variety of environmental situations.

It is a still further object to provide sealing apparatus and methods whereby relatively unskilled personnel may use the apparatus simply and effectively.

In accordance with the above objects, provision for a reuseable integral sampling tube gives rise to more specific operational features, which relate to reuse of the total package. That is, given a reuseable tube, the possibility is created for a total reuseable package, including tube hardware, absorbent material, and apparatus for holding the absorbent material within the tube. It is accordingly a further object of the present invention to provide a gas sampling configuration which is amenable to direct and total withdrawal of the sampled gases, while maintaining the integrity of the configuration, whereupon the integral configuration may then be reused.

SUMMARY OF THE INVENTION

The present invention involves use of a metallic tubular member, provided with threads at either end for receipt of sealing screws. The extremities of the tube are machined with labyrinth ridges, which are coined into a lead washer between the tube and the screw cap for sealing engagement. Within the tube, a wire form holds the charcoal in place during shipment and use, and furthermore provides a convenient means for removal and analysis. In one embodiment, the wire form constitutes an elongated "rake" adapted to the shape of the tube, while in another plural wire mesh discs, each provided with removal pins or pegs, are wedged within the tube. The threaded ends of the tube are conveniently adapted for interconnection with other tubes, or for connection with flexible tubing.

In an alternative embodiment, a metallic tube is provided with a carbon charge, and plugs of ceramic, glass, sintered metal or the like, are press fit into the tube on both sides to hold the charcoal firmly in place. Once gas samples are taken, the tube is placed in a jig and heat conduction occurs between the jig, the tube, and the plugs. Helium is passed through the assembly, is heated directly by the tube and plug, and scrubs the sampled gas. The helium with sampled gases is removed for analysis.

DESCRIPTION OF THE DRAWINGS

FIG. 6a and 6b show an alternative, totally reuseable embodiment of the present invention; and FIG. 7 shows an advantageous configuration for withdrawal of gases from the FIG. 6a embodiment.

FIGS. 8a through 8c show alternative configurations for the plugs of FIGS. 6a and 6b.

DETAILED DESCRIPTION

Figure 1:
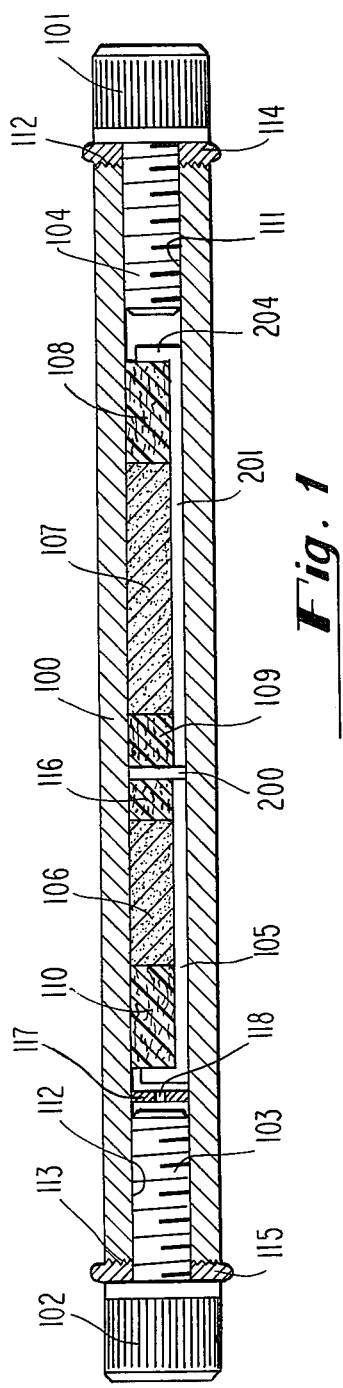
FIG. 1 shows a cross sectional view of a first embodiment of a cartridge embodying the principles of the present invention.

The cross sectional view of FIG. 1 sets forth a gas sampling cartridge embodying the principles of the present invention. A tubular metallic cylinder 100, advantageously composed of aluminum or other inert material, is provided on its inner surface at either extremity with threads 111 and 112, which in turn receive a pair of sealing screws 101 and 102, respectively. The screws are provided with hexagonal indentations on their inner surface (not shown) adapted for tightening by means of an allen wrench, or the like. The threads 111 and 112 may be tapped to receive the complementary screws 103 and 104 such that they provide a relatively tight seal for the cartridge. Alternatively, external threads and a complementary cap may be utilized.

Figure 2:
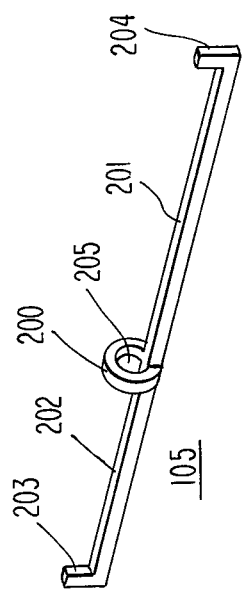
FIG. 2 shows a wire form useful for holding the charcoal in place during use, and for removal of the charcoal thereafter.

To promote the seal still further, one or more ridges 112 and 113 are machined to the extreme ends of the tube 110, advantageously in labyrinth configuration. Then, washers 114 and 115, composed of inert malleable material such as lead, complete the seal, with the ridges 112 and 113 being coined into the washers 114 and 115 as the sealing screws 101 and 102 are tightened, to provide a hermetic seal for the cartridge. In a preferred embodiment, the washers 114 and 115 have a diameter substantially equal to that of the tube and the screw heads 101 and 102, but are deformed outwardly, as shown, when the screws 101 and 102 are tightened down. The user then may effectively utilize the outward protrusion of the washers 114 and 115 beyond the diameter of the tube 100 as an indication that the tube effectively is sealed. Within the cartridge is a wire form, generally designated 105 and shown in perspective in FIG. 2. The form includes an annular portion 205 which conforms substantially to the interior of the tube 100. Depending outwardly from the annular portion 200 are elongated portions 201 and 202 which preferably are straight from end to end when the form 105 is inserted into the cartridge. The plugs of inert fibrous material such as glass wool 109 or 116 are inserted against the annular portion 200. Next, predetermined amounts of charcoal 106 and 107 are placed in the tube 100, followed by outer plugs or glass wool 108 or 110, respectively. When the charcoal and wool combinations are in place, the ends of the longitudinal wire portions 201 and 202 are crimped upwardly to form flange-like portions 203 or 204, yielding the configuration shown for the wire form 105 in FIGS. 1 and 2. Assembled in such a fashion, the wire form 105 functions to fix the position of the charcoal 106 and 107 and glass 108 and 110 within the tube, during shipping and use. Afterward, for analysis purposes, the wire form 105 conveniently serves as a rake to facilitate withdrawing the sample laden charcoal 106 and 107 from the tube for analysis.

The configuration shown for the charcoal 106 and 107 within the tube is conventional, with the larger charge of charcoal 107 functioning as the primary adsorber, and with the secondary charge 106 conventionally functioning to make certain that all gas has been absorbed in the primary charcoal. The plugs of glass wool 108, 109, 116 and 110 also function in conventional fashion to maintain the charcoal charges in position, but to permit the passage of gases through the tube 100. Utilization of the wire form 105 insures such proper function of the glass wool plugs, and furthermore prevents loosening and channeling of the charcoal whereby gases to be sampled might escape the cartridge.

In the embodiment set forth, activated charcoal is utilized as the gas sampling medium, but it is to be understood that other materials might also be used as is known in the art. For example, silica gel, alumina, or molecular sieve materials may also be advantageously use. Likewise, the gas capturing function is alternatively described herein as absorption or adsorption, in that either sort of sampling may be used, depending upon the medium employed. To this end, the terms "absorption" and "adsorption" are used interchangeably herein, since both processes are well understood and equally applicable to the present invention. Furthermore, alternative materials to glass wool might also be used in substitution for plugs 108, 109, 116 and 110, as is known in the art.

The embodiment of FIG. 1 also is provided with a means 117 for restricting air flow through the tube. Specifically, the means shown in a disc-like block 117 in the tube, having a calibrated critical orifice 118 which is machined or cut therein. Use of the orifice 118 regulates flow to a constant, known amount, and thereby eliminates the need for a complex regulator or flow controller downstream of the cartridge. Alternative blockage devices include labyrinth passageways, millipore material, or the like.

Figure 3A:
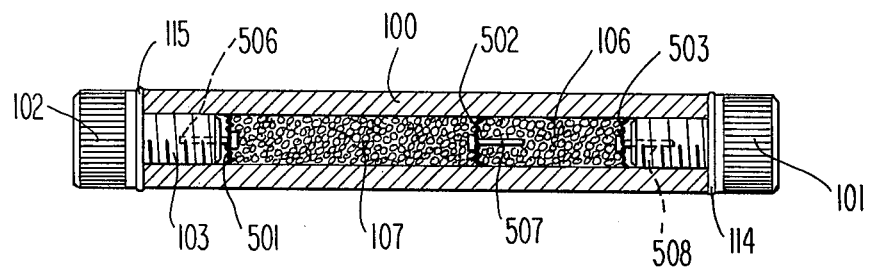
FIG. 3a shows a cross sectional view of an alternative embodiment of the principles of the present invention.
Figure 3B:
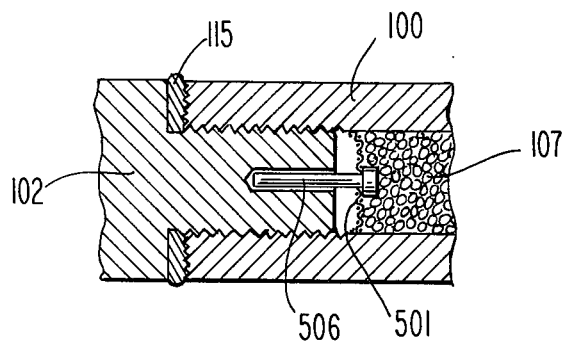
FIGS. 3b and 3c show detail views thereof.
Figure 3C:
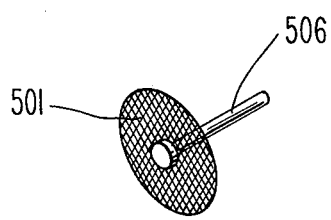

An alternative embodiment of the principles of the present invention is shown in FIGS. 3a through 3c. Those figures set forth a sampling tube generally similar to that shown in FIG. 1, except that the wire form 105 of FIG. 1 embodiment is replaced by difference apparatus for maintaining the charcoal or other absorption materials in place within the tube. Specifically, the metallic tube 100 is provided with screw on caps 101 and 102 which seal at either end of the tube 110 by means of malleable washers 114 and 115. The charges of charcoal 106 and 107 are held into place, however, by means of wire mesh discs 501, 502, and 503. Each mesh disc has at least a portion having a slightly larger diameter than the inner diameter of the tube 100, and is constituted of a metal which is substantially inert to the gases being sampled. In a preferred embodiment, the discs 501, 502, and 503 are made of 60 mesh stainless steel screen. Hence, once the screen is introduced into the tube, the "long diameter" wire edges from the screen deform slightly and "bite" into the inner periphery of the softer aluminum tube 100, thereby maintaining the screen in position, as shown in FIG. 3b. Proper choice of the screen mesh enables the charcoal 106 and 107 to be held in position merely by the screen discs 501 through 503, and obviates the need for packing materials such as 108, 109, 110, and 116 of FIG. 1. Of course, if desired, those packing materials may be also used in the embodiment of FIG. 3a.

As shown for example in FIG. 3c, each of the mesh discs 501, 502, and 503 is provided with a peg or pin 506, 507, and 508, by which the screen may be removed whenever it is desired that the charcoal be withdrawn. As shown in FIG. 3b, the screw portion of each cap 101 and 102 is provided with a suitable indentation to accommodate the withdrawal pins 506 and 508 of the end screens 501 and 503.

In a preferred mode of utilization, the cartridge is shipped prior to usage with the sealing screws 101 and 102 lightly hand tightened, whereupon the user removes the screws and employs the desired sampling procedures. When the sampling is completed, the screws 101 and 102 with the lead washers 114 and 115 are applied, and tightened until the labyrinth ridges 112 and 113 are coined into the washers 114 and 115, and the washers are deformed outwardly as set forth hereinbefore. Thereupon, the cartridge is hermetically sealed, and may be shipped for analysis without ancillary packing such as dry ice. The rigid structure, together with the wire forms, insures that the interior will not be substantially disturbed prior to analysis.

Thereafter, the tube 100 and sealing mechanisms 101 and 102 may advantageously be purified, if necessary, and reused.

Figure 5:
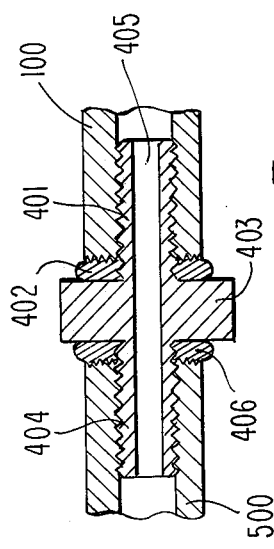
FIG. 5 shows a connector for coupling sequences of the cartridges together, as desired.

In addition to the foregoing features of the present invention, still further advantages accrue. First, it is conceivable for some applications that the exposure would be so great that the standard charcoal charge for a given cartridge would become saturated prior to termination of the exposure time. For such an eventuality, embodiments of the present invention may be coupled together such as set forth in FIG. 5. The adapter of FIG. 5 includes threaded portions 401 and 404 which mate with the threads on the interior of the respective tubes to be stacked, 100 and 500. A radial flane 403 promotes sealing registry of the tubes. As is shown, lead washers 402 and 406 may be utilized, or alternatively a teflon gasket may be use. With this approach, any number, as desired, of the cartridges may be cascaded.

Figure 4:
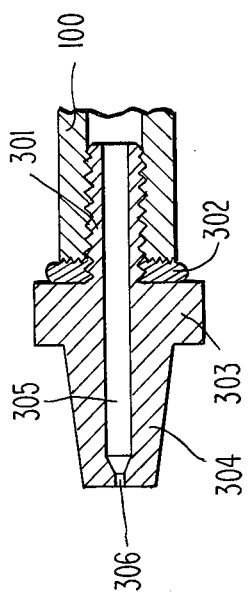
FIG. 4 shows an adapter for connecting the cartridge to flexible tubing.

The same approach may be utilized to mate the tube with a small vacuum hose pump or the like. Such apparatus is shown in FIG. 4, wherein a first threaded protuberance 301 extends into the tube 100, a radial flange assures sealable registry of the adapter, and a tapered portion 304 permits connection to the hose. A channel 305 couples the interior of the tube 100 to the hose. As an alternative to use of the blocking means 117 of FIG. 1, the adapter of FIG. 4 may advantageously be provided with a similar orificed block 306 to restrict air flow.

FIG. 6a and 6b show an alternative embodiment of the present invention. Specifically, FIG. 6a shows a cross sectional view of a different carbon tube sample system, and FIG. 6b shows a cross sectional view of the sintered glass, ceramic or metallic plugs 607 and 608 of FIG. 6a, which hold the sampling absorbent medium in place. In FIG. 6a, a metallic tube 601 of generally similar composition to those set forth in FIGS. 1 and 3 is provided at either end with threaded portions for receipt of sealing caps 602 and 604. Advantageously, the tube 601 also defines labyrinth grooves at opposite ends, and malleable washers 603 and 605 are interposed between the tube 601 and the end screw seals 602 and 604. In this respect, the embodiment of FIG. 6a is similar to those previously set forth herein.

As to the interior configuration, however, different apparatus is provided which gives rise to reuse of the entire, integral configuration of FIG. 6a. Specifically, the activated charcoal (or other suitable absorbent material) 606 is provided in a single charge (although plural charges still may be provided), and a pair of sintered aluminum barriers or plugs 607 and 608 are provided on either side of the charcoal 606. Alternatively, a metal plug 801 with fine grooves 802 or holes 803 may be used. See FIGS. 8a and 8b. Another option, as shown in FIG. 8c, utilizes a hexagonal (or other regularly shaped polygonal forms) plug pressed into a round tube. An important feature of the plugs 607 and 608 is that they form a close interference-type fit with the inner walls of the tube 601, and in fact the plugs 607 and 608 are press fit into the tube 601 permanently to compact the activated charcoal 606 at a predetermined pressure. Because the barriers 607 and 608 are press fit into the tube 601, permanant integrity of the overal configuration is assured, and the charcoal 606 is forced to stay in place, and will not channel or saturate either in use or in shipment.

In addition to the advantageous structural attributes of the configuration of FIG. 6a, use of the sintered metal plugs 606 and 608 gives rise to substantial operational facility. That is, the sintered plugs, which advantageously are composed of aluminum, but which also may be made of stainless steel or similar materials, constitute an almost perfect heat exchange, which facilitates both the sampling and the sample removal operations. Further, the press fit creates a thermally conductive joint between plugs and tube. Hence, in the sampling operation, the highly heat conductive aluminum tube 601 and the contacting plugs 607 and 608 quickly and effectively adapt thermally to room temperature, and avoid having an effect on the room air which is being drawn through the tube.

More importantly, however, the heat conductive attributes of the FIG. 6a embodiment allow for substantially total removal of the sampled gas without disassembling the tube itself, and thereby enable virtually unlimited reuse of the integral configuration. FIG. 7 shows a configuration whereby these properties of the FIG. 6 apparatus may be utilized.

In FIG. 7, an aluminum block 701 is provided with channels for receipt of heater cartridges 702 and 703, which are suitably energized through the electrical leads shown. A thermocouple may be provided in a recess 704, whereby the thermal state of the FIG. 7 configuration may be determined, and, as desired, controlled by alteration of the power provided to the heating cartridges 702 and 703. Threaded openings 715 through 718 are provided for suitable mounting of the aluminum block of 701.

A channel is provided in the block 701 intermediate the heaters 702 and 703, which is adapted to receive the tube 601 once the end screws 602 and 604 and sealing gaskets 603 and 605 are removed. As shown, the channel for the tube 601 allows the block 701 substantially to contact the entire outer surface of tube 601. Scrub gas, preferably helium, is provided at the lower portion of the block 701, advantageously by a screw connection at 711. The helium gases are then forced through a plurality of sintered discs 705 through 708, which preferably are of the same composition as the plugs 607 and 608 which maintain the charcoal 606 within the tube 601. A silicone washer 712 and a teflon disc 713 provide sealed engagement of the top and bottom of the tube 601 thereby insuring that all scrub gases will be passed through the activated charcoal 606.

The tube 601 is sealed within the block 701 by means of a fitting 709, which mates with the end threading of the tube 601, and which thereby promotes simple installation and removal of the tube 601 from the block 701. A lock screw 714 holds the fitting 709 in place against the block 701, and a valve 710 fits atop a channel which penetrates the fitting 709 to communicate with the interior of the tube 601. The valve 710 also is provided with an closable opening which accepts the needle portion 719 of a syringe 720, which at the beginning of the scrubbing operation has its piston 721 at its lower most position.

The apparatus of FIG. 7 is designed to operate as follows. Once the tube 601 is prepared for scrubbing and is mounted with fitting 709 into the block 701, cartridges 702 and 703 are energized until a steady state condition occurs at a predetermined temperature, including the tube 601 and the plugs 607 and 608. Helium is provided at 711, and is heated as it passes through the tube 601 and the sintered blocks 608, and in its heated condition scrubs sampled hydrocarbon gases from the activated charcoal 606. Pressure from the helium forces these gases up through the fitting 709 and the valve 710, and into the syringe 720, thereby raising the plunger 721 and providing a ready reference of the volumes involved. Whenever desired, the syringe 720 is removed and its content gases may be injected for analysis in a gas chromatograph or the like.

The foregoing embodiments are submitted as preferred illustrations of the principles of the present invention. It is to be understood that numerous alternatives may occur to those of ordinary skill in the art, without departure from the spirit or the scope of the present invention.

We claim:

1. A cartridge for sampling ambient gases comprising:
a rigid metallic cylindrical thermally conductive tube, inert to the ambient gases and provided with a threaded portion at each end;
a predetermined charge of gas absorber material within said tube;
first and second rigid, integral, thermally conductive plugs having a rigid substantially permanent force fit in thermally conductive relation with the interior of said tube, said plugs having openings therethrough to permit flow of gases through said plugs and said tube, said plugs permanently enclosing and compressing said absorber material in said tube; and
sealing screw means for each end of said tube.

2. A cartridge as describe in claim 1 wherein said tube is provided at each extreme end with a raised ridge, and wherein said cartridge further comprises a malleable washer between each said extreme end and a corresponding one of said sealing screws, said ridges being sealably coined into said washers and said washers being respectively radially displaced beyond the outer surface of said tube when said sealing screws are respectively tightened, the radial deformation of said washers providing an indication of the seal of said cartridge.

3. A cartridge as described in claim 1 wherein said plugs are composed of a material selected from the group consisting of sintered metal, ceramic, and glassy materials.

4. A cartridge as described in claim 1 wherein said material of said plugs is selected from the group consisting of sintered aluminum and sintered stainless steel.

5. A method for collecting ambient gases for analysis comprising the steps of:
providing a rigid, thermally conductive metallic tube;
providing a predetermined charge of gas absorber material in said tube;
compacting said absorber within said tube to a predetermined pressure by press fitting a pair of thermally conductive sintered metal plugs in said tube against said absorber material while maintaining a thermally conductive contact joint between said plugs and said tube;
passing ambient gases through said tube, said plugs, and said absorber material at a predetermined rate for a predetermined time, thereby sampling said ambient gases:
heating said tube and said plugs in an integral condition with said absorber material enclosed therein to a predetermined temperature;
passing a predetermined volume of scrub gas through said heated tube and plugs, thereby heating said scrub gas and promoting removal of sampled ambient gases from said absorber material; and
collecting said scrub gas and ambient gases.

6. A method as described in claim 5 wherein said heating step comprises placing said tube in contact with a heat source, and energizing said source to develop a predetermined amount of heat.

7. A cartridge for sampling ambient gases by drawing them through a gas absorber for a specified duration at a specified rate comprising:
a. an elongated cylindrical tube composed of a rigid, nonbreakable material inert to the ambient gases, said tube being provided with a threaded portion at each end;
b. sealing screw means for each end of said tube;
c. a predetermined quantity of said gas absorber within said tube; and
d. means for holding said absorber in a fixed position within said tube, said means for holding including
i. an annular portion conforming to the interior portion of said tube and at least one elongated member depending from said annular portion, and terminating in a flange, and
ii. inert fibrous plugs respectively adjacent said annular portion and said flange and enclosing said absorber material between said annular portion and said flange
e. whereby said absorber is maintained in fixed relationship with said tube and is removable from said tube in association with said means for holding.

8. A cartridge as described in claim 7 wherein said structural means includes two of said elongated members depending in opposite directions from said annular portion, each elongated member terminating in one of said flanges an enclosing absorber material.

9. A cartridge for sampling ambient gases by drawing them through a gas absorber for a specified duration at a specified rate comprising:

a. an elongated cylindrical tube composed of a rigid, nonbreakable material inert to the ambient gases, said tube being provided with a threaded portion at each end;
b. sealing screw means for each end of said tube;
c. a predetermined quantity of said gas absorber within said tube; and
d. means for holding said absorber in a fixed position within said tube, said means for holding comprising a plurality of wire mesh discs each conforming to and having an interference fit within said tube, said absorber being held within said tube between respective ones of said discs, each of said discs being penetrated by an elongated pin for removal of the disc by grasping the corresponding pin.

10. A reusable cartridge for sampling ambient gases by drawing them through a predetermined quantity of gas absorber for a specified duration at a specified rate comprising:

an elongated thermally conductive cylindrical tube composed of rigid, nonbreakable material inert to the gases being sampled, said tube being provided with a threaded portion at each end;

sealing screw means for each end of said tube; and means for permanently and rigidly holding said absorber in a fixed compacted position with said tube, said means for holding being in thermally conductive relation with said tube.

11. A cartridge as described in claim 10 and further comprising malleable sealing washers, radially deformable under compression, said washers being located between respective sealing screws and ends of said tube, the radial deformation of said washers providing an indication of the seal of said screws after sampling.

* * * * *